(12) United States Patent
Kang et al.

(10) Patent No.: US 10,042,256 B2
(45) Date of Patent: Aug. 7, 2018

(54) SILANE COUPLING AGENT AND METHOD OF MANUFACTURING WIRE GRID PATTERN USING THE SAME

(71) Applicant: Samsung Display Co., Ltd., Yongin-si (KR)

(72) Inventors: Min Hyuck Kang, Seoul (KR); Eun Ae Kwak, Gunpo-si (KR); Dong Eon Lee, Seoul (KR); Gug Rae Jo, Asan-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 0 days.

(21) Appl. No.: 15/168,665

(22) Filed: May 31, 2016

(65) Prior Publication Data

US 2017/0090285 A1    Mar. 30, 2017

(30) Foreign Application Priority Data

Sep. 30, 2015 (KR) ........................ 10-2015-0137627

(51) Int. Cl.
| | | |
|---|---|---|
| *G03F 7/075* | (2006.01) | |
| *G03F 7/004* | (2006.01) | |
| *C07F 7/18* | (2006.01) | |
| *G02B 5/30* | (2006.01) | |
| *C23F 1/02* | (2006.01) | |
| *C23F 1/00* | (2006.01) | |
| *G03F 7/00* | (2006.01) | |

(52) U.S. Cl.
CPC .......... *G03F 7/0751* (2013.01); *C07F 7/1828* (2013.01); *C07F 7/1868* (2013.01); *C23F 1/00* (2013.01); *C23F 1/02* (2013.01); *G02B 5/3058* (2013.01); *G03F 7/0002* (2013.01); *Y02P 20/582* (2015.11)

(58) Field of Classification Search
None
See application file for complete search history.

(56) References Cited

U.S. PATENT DOCUMENTS

| | | | | |
|---|---|---|---|---|
| 3,431,129 | A * | 3/1969 | Ismail | ............... C08K 5/549 106/192.1 |
| 4,514,479 | A * | 4/1985 | Ferrante | ............... G02B 5/32 216/24 |
| 4,818,661 | A * | 4/1989 | Taylor | ............... G03F 1/20 205/135 |

(Continued)

FOREIGN PATENT DOCUMENTS

| | | |
|---|---|---|
| JP | 2003-292496 | * 10/2003 |
| JP | 2008-050321 | *  3/2008 |

(Continued)

*Primary Examiner* — Martin J Angebranndt
(74) *Attorney, Agent, or Firm* — H.C. Park & Associates, PLC

(57) ABSTRACT

A method of manufacturing a wire grid pattern includes providing a laminate having a base member, a metal layer disposed on the base member, a mask layer disposed on the metal layer and containing a metal oxide, an adhesive layer disposed on the mask layer, and a patterned resin layer disposed on the adhesive layer and formed by irradiation of first light; and irradiating the laminate with second light. The adhesive layer may comprise a silane coupling agent.

8 Claims, 14 Drawing Sheets

(56) References Cited

U.S. PATENT DOCUMENTS

| | | | | |
|---|---|---|---|---|
| 5,951,880 | A * | 9/1999 | Chen | G11B 5/6005 |
| | | | | 216/100 |
| 6,210,846 | B1 * | 4/2001 | Rangarajan | G03F 7/40 |
| | | | | 257/E21.027 |
| 6,746,822 | B1 * | 6/2004 | Rangarajan | G03F 7/265 |
| | | | | 257/E21.026 |
| 9,343,553 | B2 * | 5/2016 | Lee | G03F 7/0751 |
| 2003/0230550 | A1 * | 12/2003 | Chang | G01L 9/0042 |
| | | | | 216/59 |
| 2011/0165412 | A1 | 7/2011 | Ye et al. | |
| 2012/0009325 | A1 * | 1/2012 | Storment | A61F 2/91 |
| | | | | 427/2.25 |
| 2013/0270223 | A1 * | 10/2013 | Lee | G03F 7/031 |
| | | | | 216/24 |
| 2015/0079351 | A1 | 3/2015 | Atasoy et al. | |
| 2017/0348729 | A1 * | 12/2017 | Kwak | B05D 1/005 |

FOREIGN PATENT DOCUMENTS

| | | | |
|---|---|---|---|
| KR | 2005017871 | * | 2/2005 |
| KR | 2005038243 | * | 4/2005 |
| WO | 2011-066450 | | 6/2011 |

* cited by examiner

FIG. 2A
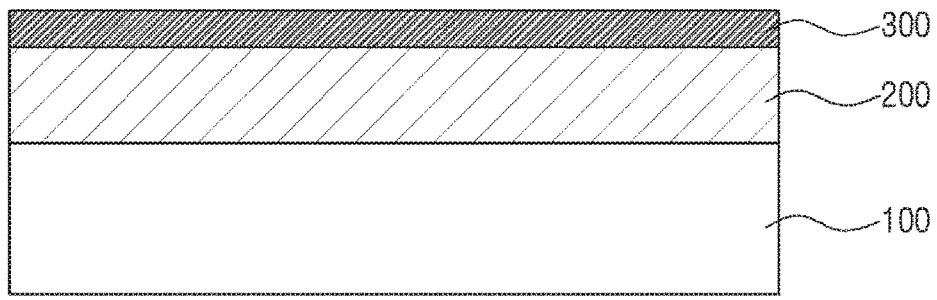
FIG. 2B
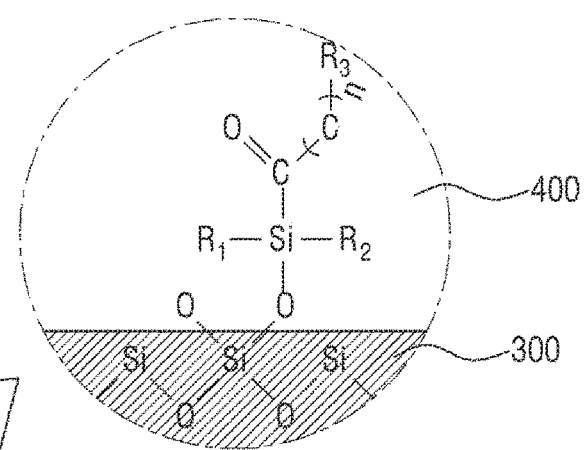
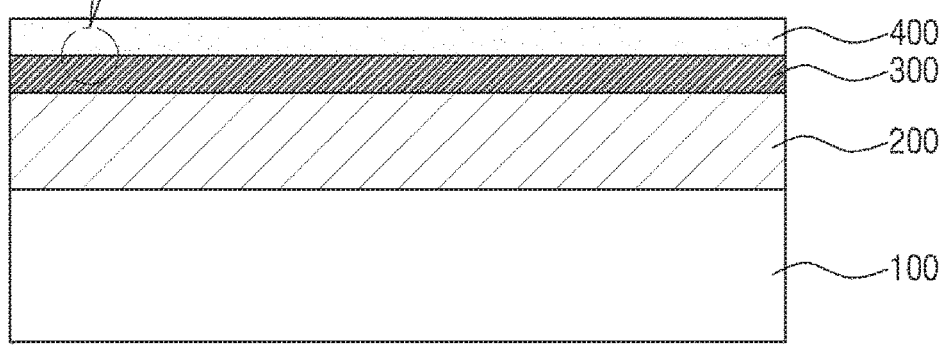

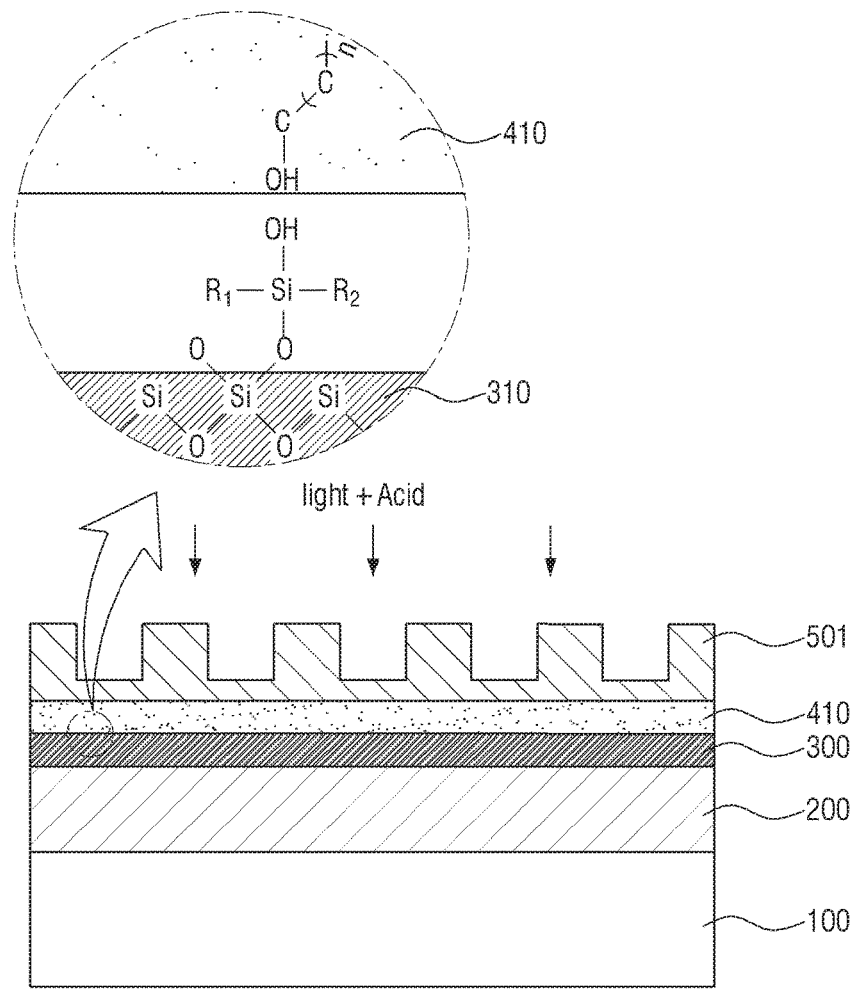

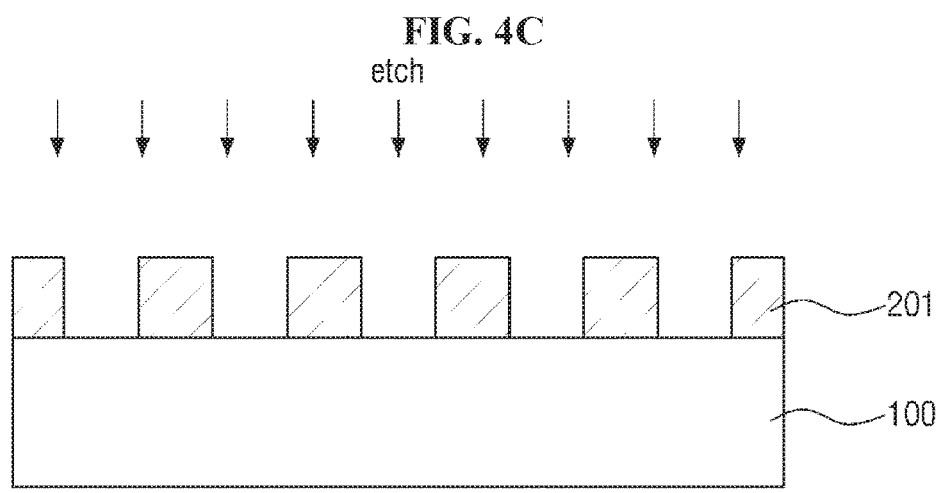

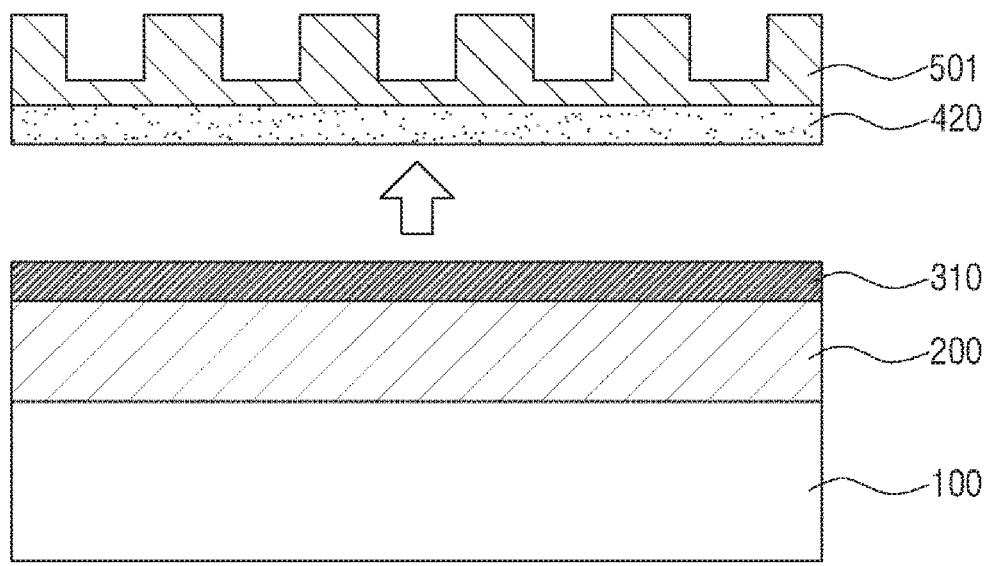
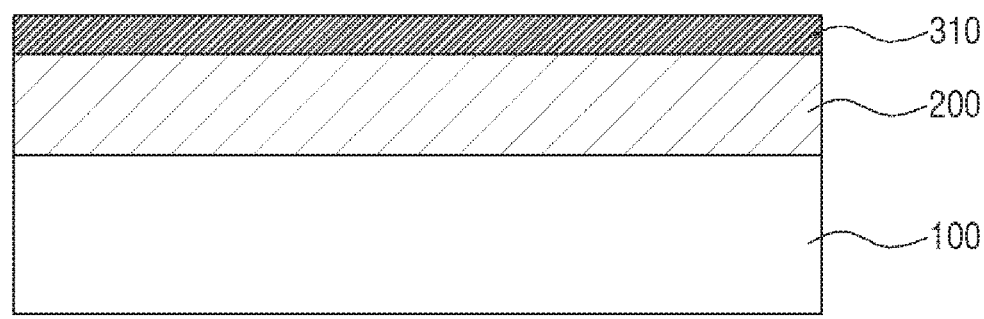

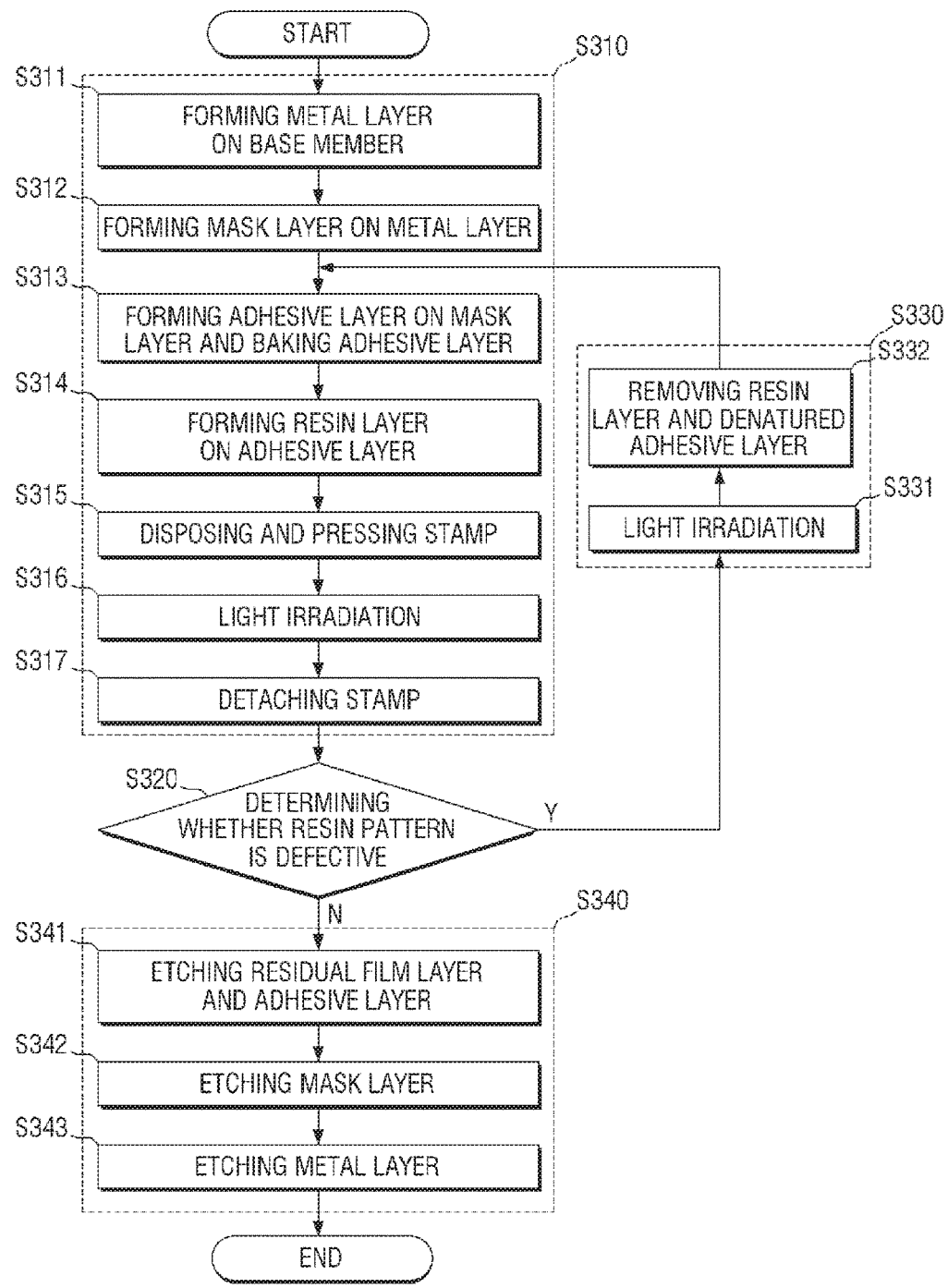

SILANE COUPLING AGENT AND METHOD OF MANUFACTURING WIRE GRID PATTERN USING THE SAME

CROSS-REFERENCE TO RELATED APPLICATION

This application claims priority from and the benefit of Korean Patent Application No. 10-2015-0137627, filed on Sep. 30, 2015, which is hereby incorporated by reference for all purposes as if fully set forth herein.

BACKGROUND

Field

Exemplary embodiments relate to a silane coupling agent and a method of manufacturing a wire grid pattern using the silane coupling agent.

Discussion of the Background

A wire grid pattern is collectively referred to as a wire grid structure in which metal wires protruding in the shape of stripes are arranged at predetermined intervals.

A wire grid polarizer has polarization separation characteristics of reflecting polarized light parallel to a wire grid direction and transmitting polarized light perpendicular to the wire grid direction. Therefore, when the wire grid polarizer is used as a polarizing plate of a liquid crystal display panel, the light reflected from the wire grid polarizer is incident upon a backlight unit to be recycled, thereby improving light efficiency.

Since the wire grid pattern has a width and cycle of only several tens to several hundreds of nanometers, a very precise process is required. An electron beam lithography process, a block copolymer patterning process, or a nano-imprint lithography process are exemplary means for forming a wire grid pattern. In particular, forming a wire grid pattern using a nano-imprint lithography process can also control nano-sized patterns, is advantageous in manufacturing a large-size wire grid pattern, and is effective in terms of costs.

The above information disclosed in this Background section is only for enhancement of understanding of the background of the inventive concept, and, therefore, it may contain information that does not form the prior art that is already known in this country to a person of ordinary skill in the art.

SUMMARY

In a conventional nano-imprint lithography process, a metal layer, a mask layer, and a resin layer are disposed on a base member, a grid pattern is transferred to the resin layer using a stamp, the stamp is removed, and the metal layer is etched using the resin pattern as an anti-etching film so as to form a wire grid pattern. In this case, there is a problem in that at least a part of the resin pattern is stripped together with the stamp during removing the stamp, and thus a previously-designed pattern cannot be fully formed. Such a problem becomes more serious with an increase in pattern size precision.

Further, in order to perform a rework process of processing the nano-imprint lithography process by removing the defective resin pattern and forming the resin layer again, it is difficult to completely remove the defective resin pattern such that no foreign matter remains as the resin pattern is first formed on the surface of the mask layer, and the time and additional process taken to remove the defective resin pattern may cause the deterioration in processibility of a wire grid pattern.

Exemplary embodiments provide a method of manufacturing a wire grid pattern, which can prevent a resin pattern in a nano-print lithography process from being stripped during removal of a stamp.

Exemplary embodiments also provide a method of manufacturing a wire grid pattern, which includes a rework process for easily removing a defective resin pattern.

Exemplary embodiments further provide a silane coupling agent, which can be used to improve the method of manufacturing a wire grid pattern.

Additional aspects will be set forth in the detailed description which follows, and, in part, will be apparent from the disclosure, or may be learned by practice of the inventive concept.

An exemplary embodiment discloses a method of manufacturing a wire grid pattern that includes providing a laminate having a base member, a metal layer disposed on the base member, a mask layer disposed on the metal layer and containing a metal oxide, an adhesive layer disposed on the mask layer, and a patterned resin layer disposed on the adhesive layer and formed by irradiation of first light; and irradiating the laminate with second light.

An exemplary embodiment also discloses a method of manufacturing a wire grid pattern including providing a laminate having a base member, a metal layer disposed on the base member, a mask layer containing a metal oxide and disposed on the metal layer, an adhesive layer disposed on the mask layer, and a patterned resin layer disposed on the adhesive layer; treating the laminate with a base; and treating the laminate with an acid.

An exemplary embodiment further discloses a silane coupling agent. The silane coupling agent is represented by Chemical Formula 1-1, Chemical Formula 2-1, or Chemical Formula 3-1 below:

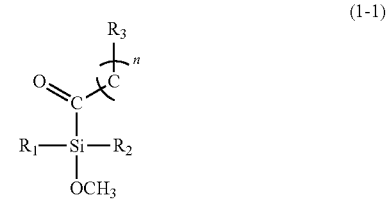

(1-1)

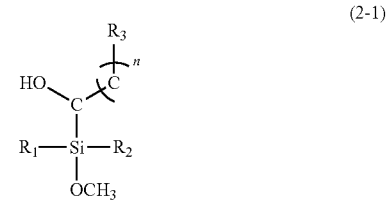

(2-1)

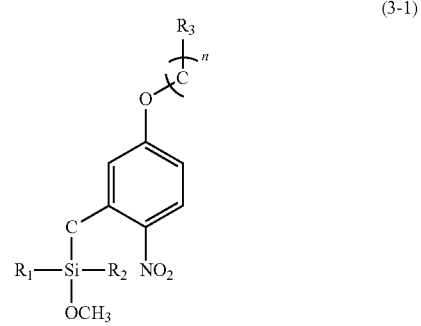

(3-1)

wherein in the formula 1-1, $R_1$ and $R_2$ are each independently any one of —$CH_3$, —$OCH_2CH_3$, —$OCH_3$, and a functional group represented by Chemical Formula 1-2 below; in the formula 2-1, $R_1$ and $R_2$ are each independently any one of —$CH_3$, —$OCH_2CH_3$, —$OCH_3$, and a functional group represented by Chemical Formula 2-2 below; and in the formula 3-1, $R_1$ and $R_2$ are each independently any one of —$CH_3$, —$OCH_2CH_3$, —$OCH_3$, and a functional group represented by Chemical Formula 3-2 below,

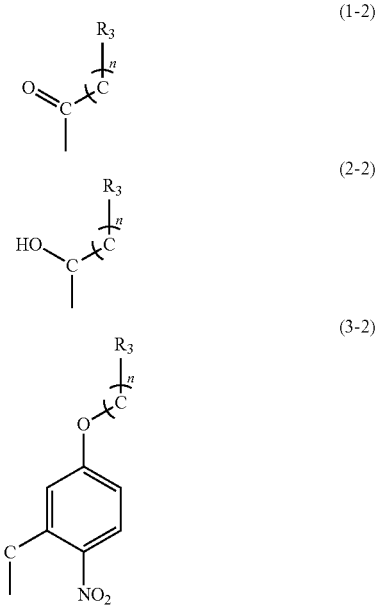

and in the formulae 1-1, 1-2, 2-1, 2-2, 3-1, and 3-2, $R_3$ is any one of an acrylate group and a methacrylate group, and n is an integer of 1 to 10.

The foregoing general description and the following detailed description are exemplary and explanatory and are intended to provide further explanation of the claimed subject matter.

BRIEF DESCRIPTION OF THE DRAWINGS

The accompanying drawings, which are included to provide a further understanding of the inventive concept, and are incorporated in and constitute a part of this specification, illustrate exemplary embodiments of the inventive concept, and, together with the description, serve to explain principles of the inventive concept.

FIG. 2A, FIG. 2B, FIG. 2C, FIG. 2D, and FIG. 2E are cross-sectional views showing a process of forming a resin pattern of FIG. 1 in a stepwise manner.

FIG. 3A, FIG. 3B, and FIG. 3C are cross-sectional views showing a process of removing a resin pattern of FIG. 1 in a stepwise manner.

FIG. 4A, FIG. 4B, and FIG. 4C are cross-sectional views showing a process of forming a metal pattern of FIG. 1 in a stepwise manner.

FIG. 6A, FIG. 6B, and FIG. 6C are cross-sectional views showing a process of removing a resin pattern of FIG. 5 in a stepwise manner.

FIG. 7 is a flowchart showing a method of manufacturing a wire grid pattern according to still another exemplary embodiment.

DETAILED DESCRIPTION OF THE ILLUSTRATED EMBODIMENTS

Figure 1:
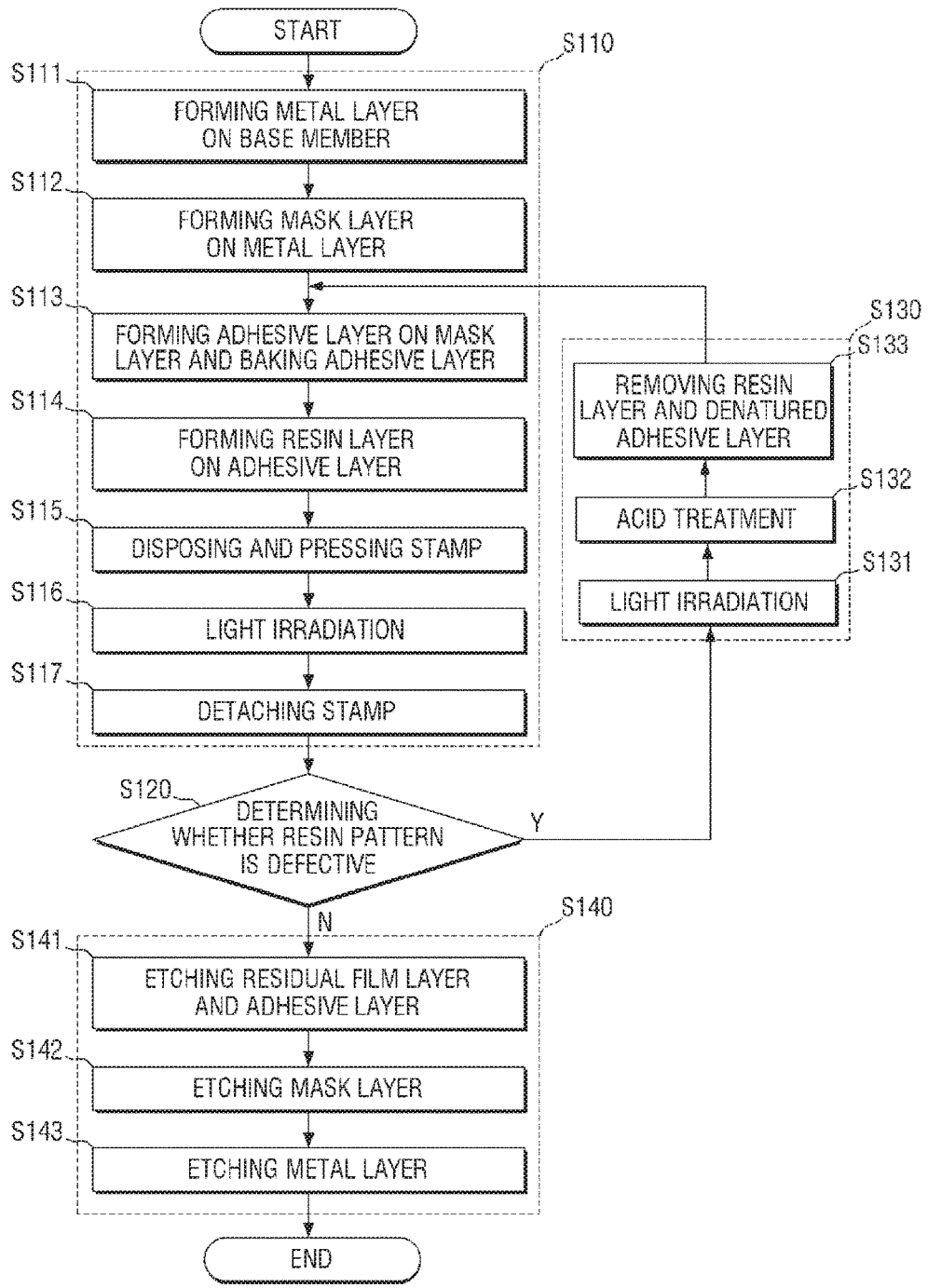
FIG. 1 is a flowchart showing a method of manufacturing a wire grid pattern according to an exemplary embodiment.

In the following description, for the purposes of explanation, numerous specific details are set forth in order to provide a thorough understanding of various exemplary embodiments. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments.

In the accompanying figures, the size and relative sizes of layers, films, panels, regions, etc., may be exaggerated for clarity and descriptive purposes. Also, like reference numerals denote like elements.

When an element or layer is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. Like numbers refer to like elements throughout. As used herein, the term "and/or" includes any and all combinations of one or more of the associated listed items.

Although the terms first, second, etc. may be used herein to describe various elements, components, regions, layers, and/or sections, these elements, components, regions, layers, and/or sections should not be limited by these terms. These terms are used to distinguish one element, component, region, layer, and/or section from another element, component, region, layer, and/or section. Thus, a first element, component, region, layer, and/or section discussed below could be termed a second element, component, region, layer, and/or section without departing from the teachings of the present disclosure.

Spatially relative terms, such as "beneath," "below," "lower," "above," "upper," and the like, may be used herein for descriptive purposes, and, thereby, to describe one element or feature's relationship to another element(s) or feature(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof.

Various exemplary embodiments are described herein with reference to sectional illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not be construed as limited to the particular illustrated shapes of regions, but are to include deviations in shapes that result from, for instance, manufacturing. As such, the regions illustrated in the drawings are schematic in nature and their shapes are not intended to illustrate the actual shape of a region of a device and are not intended to be limiting.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and will not be interpreted in an idealized or overly formal sense, unless expressly so defined herein.

FIG. 1 is a flowchart showing a method of manufacturing a wire grid pattern according to an exemplary embodiment. FIGS. 2A, 2B, 2C, 2D, and 2E are cross-sectional views showing a process of forming a resin pattern of FIG. 1 in a stepwise manner.

Referring to FIG. 1, the method of manufacturing a wire grid pattern according to an exemplary embodiment includes the steps of: forming a resin pattern (110); determining whether the resin pattern is defective (S120); removing the resin pattern in order to perform a reworking when it is determined that the resin pattern is defective (S130); and forming a metal pattern (S140).

Referring to FIGS. 1 and 2A, first, a base member 100 is prepared. The base member 100, for example, may be a transparent or opaque insulating substrate, such as a silicon substrate, a glass substrate, or a plastic substrate, but exemplary embodiments are not limited thereto. The base member 100 means an underlayer substrate for forming a wire grid pattern.

Next, a metal layer 200 is formed on the base member 100 (S111). The metal layer 200 contains a metal material having excellent reflectivity and/or conductivity and is formed into a wire grid pattern through subsequent processes. For example, the metal layer 200 may contain one or more of aluminum, gold, silver, copper, chromium, iron, nickel, molybdenum, titanium, oxides thereof, and alloys thereof. FIG. 2A shows a case that the metal layer 200 is a single layer made of one of the metal materials. However, in some embodiments, the metal layer 200 may be a multi-layer structure having a plurality of layers, and, in this case, each of the layers may be individually made of one of the metal materials. The method of forming the metal layer 200 on the base member 100 may be performed by deposition, such as chemical vapor deposition (CVD) or physical vapor deposition (PVD), or sputtering, but exemplary embodiments are not limited thereto.

Next, a mask layer 300 is formed on the metal layer 200 (S112). The mask layer 300 may be made of an inorganic insulating material, such as silicon nitride ($SiN_x$) or silicon oxide ($SiO_x$), or other metal oxides. As the material of the mask layer 300, a material having high etching selectivity to the metal layer 200 may be selected. In an exemplary embodiment, the metal layer 200 may be made of aluminum, and the mask layer may be made of or silicon oxide ($SiO_x$). When the etching selectivity of the metal layer 200 and the mask layer 300 increases, the consumption of the mask layer 300 during etching the metal layer 200 in order to form a wire grid pattern can be minimized, and thus it is possible to form a precise nano-sized wire grid pattern. In some embodiments, the mask layer may be a multi-layer structure having a plurality of layers.

Next, referring to FIGS. 1 and 2B, an adhesive layer 400 is formed on the mask layer 300, and is baked (S113). The adhesive layer 400 serves to bond the mask layer 300 therebeneath and the resin layer 500 thereon. When the bonding force between the resin layer 500 and a layer disposed therebeneath is not sufficient, the resin layer 500 may be stripped during a process of removing a stamp after imprinting. The stripping of the resin layer 500 can be previously prevented by interposing the adhesive layer 400 between the mask layer 300 and the resin layer 500.

The adhesive layer 400 may contain a silane coupling agent. The silane coupling agent according to an exemplary embodiment includes a compound represented by Chemical Formula 1-1 below.

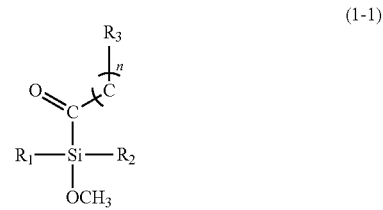

(1-1)

In the formula 1-1, $R_1$ and $R_2$ are each independently any one of —$CH_3$, —$OCH_2CH_3$, —$OCH_3$, and a functional group represented by Chemical Formula 1-2 below.

(1-2)

In the formulae 1-1 and 1-2, $R_3$ is any one of an acrylate group and a methacrylate group, and n is an integer of 1 to 10.

A composition containing the silane coupling agent is applied onto the mask layer 300 in which a hydroxyl group is exposed on the surface thereof, and is then baked to induce a covalent bond between one molecular end (for example, —$OCH_3$) of the silane coupling agent and at least a part of the hydroxyl group (—OH) of the surface of the mask layer 300 as well as to remove a solvent in the composition, thereby forming a strong bond between the adhesive layer 400 and the mask layer 300.

Figure 2C:
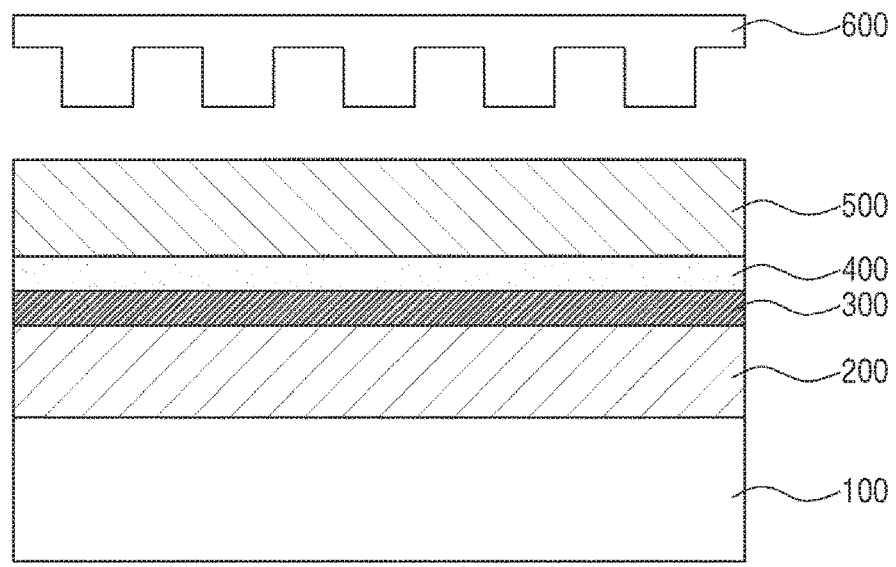

Next, referring to FIGS. 1 and 2C, the resin layer 500 is formed on the adhesive layer 400. The resin layer 500 may be made of a UV-curable resin material including an acrylate-based material, such as pentatetrathritol (meth)acrylate, dipentatetrathritol (meth)acrylate, polyester (meth)acrylate, or urethane (meth)acrylate. The resin layer 500 may be formed by applying the resin material onto the adhesive layer 400. The resin layer 500 may be formed to a thickness of 50 nm to 500 nm, but embodiments are not limited thereto. The resin layer 500 may be formed to have a thickness to such a degree that a residual film layer is formed between the adhesive layer 400 and a pattern formed on the surface of the resin layer 500 in consideration of the maximum height of a pattern of a stamp 600. The resin layer 500 of FIG. 2C, which is a resin layer before curing, may have predetermined fluidity, and may be cured while or after pressing the stamp 600.

Next, the stamp 600, which is patterned to face the base member 100 sequentially provided thereon with the metal layer 200, the mask layer 300, the adhesive layer 400, and the resin layer 500, is disposed and pressed (S115). A stripe-shaped pattern, which is a reverse phase of a wire grid pattern to be manufactured, may be formed on one side of the stamp 600. The method of forming a pattern on one side of the stamp 600 may be performed by laser interference lithography, electron beam lithography, or nano-imprint lithography.

Figure 2D:
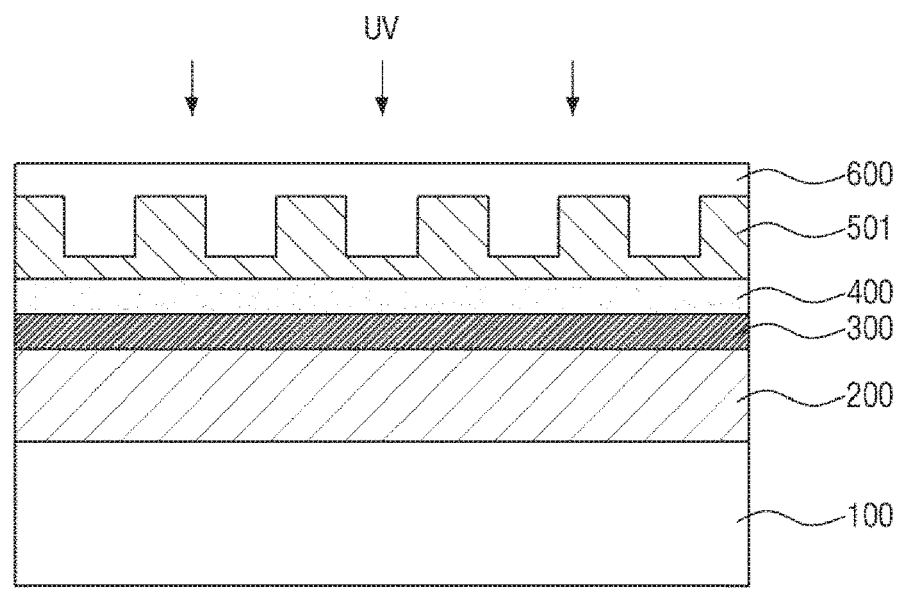

Next, referring to FIGS. 1 and 2D, an imprint process of pressing the stamp 600 to one side of the resin layer 500 to transfer a pattern of one side of the stamp 600 to one side of the resin layer 500. The resin layer 500, to which the pattern of the stamp 600 was transferred, may have a plurality of patterns and a residual film layer. That is, the stamp 600 may be pressed such that the uppermost portion of the pattern of the stamp 600 is not completely brought into contact with the surface of the adhesive layer 400 to be spaced apart from the surface thereof, and, in this case, a residual film layer may exist between the uppermost portion of the pattern of the stamp 600 and the adhesive layer 400. In some embodiments, the stamp 600 may be pressed such that the uppermost portion of the pattern of the stamp 600 is brought into contact with the surface of the adhesive layer 400, and thus the residual film layer may not exist.

The resin layer 500 with the pattern is then irradiated with light (S116) (hereinafter, first light irradiation step). In an exemplary embodiment, the light used in the first light irradiation step (S116) may be UV light having a wavelength of 350 nm to 370 nm. In the present specification, the wavelength of light refers to a center wavelength. The resin layer 500 containing a UV-curable resin material may be cured by UV irradiation, and the cured resin layer 501 can maintain the formed pattern shape even after detaching the stamp 600 and can function as a hard mask by removing the fluidity of the resin layer 500.

Further, a covalent bond is induced between an acrylate group of one molecular end of the silane coupling agent in the adhesive layer 400 and an acrylate group in the resin layer 500 by UV irradiation, thereby forming a strong bond between the adhesive layer 400 and the cured resin layer 501 that has the pattern. As described above, since the molecule of the silane coupling agent in the adhesive layer 400 forms covalent bonds together with the mask layer therebeneath and the cured resin layer 501 thereon, the bonding force between the mask layer 300 and the cured resin layer 501 can be improved through the adhesive layer 400.

Figure 2E:
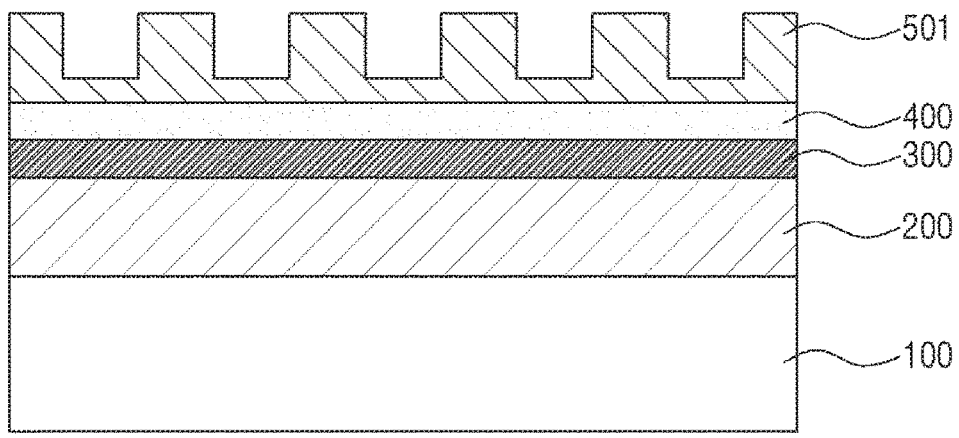

Next, referring to FIGS. 1 and 2E, the stamp 600 is removed to expose the cured resin layer 501 (S117), now a resin pattern 501, and the step (S120) of determining whether the formed resin pattern is defective is performed. As used herein, "defective" means that a pattern is not completely transferred, the resin layer 501 is not completely cured so as to maintain a perfect shape, or at least a part of the resin layer 501 or the pattern formed on the resin layer 501 is stripped off in the step of removing the stamp 600.

If it is determined that the resin pattern 501 is defective (Y, or yes), a rework process including the step of removing the defective resin pattern 501 is performed. Although the resin pattern 501 is defective, when a rework process for reusing the previously manufactured substrate by removing only the defective portion without forming a new metal layer and a new mask layer is used, the time and cost required for a process of manufacturing a wire grid pattern can be reduced, and consequently, the yield and reliability of a wire grid pattern can be improved.

Figure 3B:
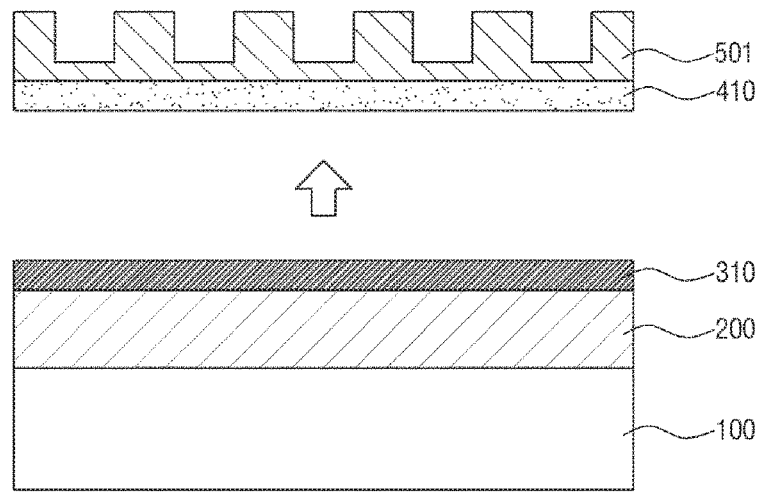
Figure 3C:
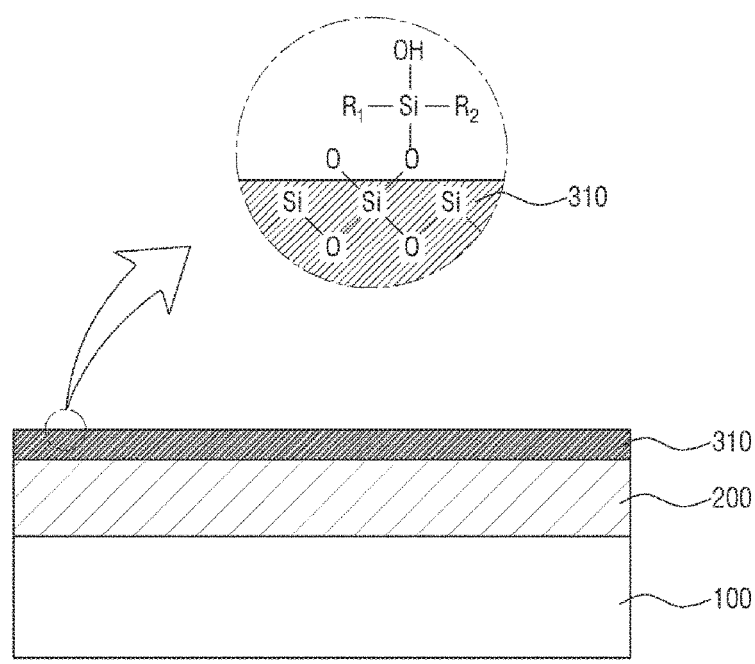

FIGS. 3A, 3B, and 3C are cross-sectional views showing a process of removing a resin pattern of FIG. 1 in a stepwise manner.

Referring to FIG. 1, the step (S130) of removing a resin pattern includes a UV irradiation step (S131), an acid treatment step (S132), and a step (S133) of removing a resin layer and a denatured adhesive layer.

Referring to FIGS. 1 and 3A, an adhesive layer is irradiated with light (S131) (hereinafter, second light irradiation step). FIG. 3A shows a case that light is emitted from above, but light may be emitted from below. The light used in the second light irradiation step (S131) may have a different wavelength from the light used in the first light irradiation step (S116). In an exemplary embodiment, the light used in the second light irradiation step (S131) may be light having a wavelength of 500 nm to 600 nm. In the present specification, the wavelength of light refers to a center wavelength. In the second light irradiation step (S131), brook rearrangement may occur in the silane coupling agent molecule in the adhesive layer 410, but exemplary embodiments are not limited thereto.

The adhesive layer is then treated with an acid reagent (S132). As the method of treating the adhesive layer with the acid reagent, a method of applying the acid reagent onto the adhesive layer or a method of dipping the adhesive layer into the acid reagent is exemplified, but exemplary embodiments are not limited thereto. The adhesive layer is denatured by the second light irradiation step (S131) and the step of treating the adhesive layer with the acid reagent, and, as shown in FIG. 3A, a part of the molecular chain derived from the silane coupling agent molecule is cut, and thus the adhesive layer 410 may be decomposed.

Specifically, when the bond between silicon (Si) and an oxygen group of end of an alkyl chain is cut, a silicon-centered molecular unit may remain while maintaining a covalent bond with a mask layer 310 therebeneath, and an alkyl chain unit occupying a majority of the adhesive layer 410 may be detached from the surface of the mask layer 310 while maintaining a covalent bond with a resin layer 501 thereon. That is, due to the denaturation of the adhesive layer 410, the mask layer 310 and the resin layer 501, which has been bonded to each other through the adhesive layer 410, lose a boding force, and thus a rework for removing the resin layer 501 may be easily performed.

Next, referring to FIGS. 1 and 3B, the resin layer 501 and the denatured adhesive layer 410 are removed (S133). As the method of removing the resin layer 501 and the denatured adhesive layer 410, a wet process of applying a solvent onto the resin layer 501 and the denatured adhesive layer 410 or dipping the resin layer 501 and the denatured adhesive layer 410 into the solvent is exemplified, but exemplary embodiments are not limited thereto. As described above with reference to FIG. 3A, the resin layer 501 and alkyl chain molecules in the adhesive layer having lost a bonding force with the mask layer 310 can be easily removed.

Then, referring to FIGS. 1 and 3C, a base member 100, a metal layer 200, and a mask layer 310 are provided in a state in which the adhesive layer and the resin layer were removed. In this case, a part of a silane coupling agent molecule including a silicon oxide unit may remain on the surface of the mask layer 310. A hydroxyl group of end of the remaining silane coupling agent molecule including a silicon oxide unit can be substantially chemically bonded with the hydroxyl group exposed on the surface of the first mask layer 300. Therefore, the mask layer 310, in which a silicon oxide unit is exposed on the surface thereof, can form a covalent bond with the adhesive layer containing a silane coupling agent and formed in the rework process although the surface composition of the mask layer 310 becomes different from that of the first mask layer 300, thereby continuing a process of manufacturing a wire grid pattern without preparing a new metal layer and a new mask layer.

Although not shown in the drawings, the step of removing a resin pattern may further include the step of cleaning the mask layer in a state in which the adhesive layer and the resin layer are removed.

Next, the step (S110) of forming a resin pattern including the step (S113) of forming an adhesive layer on the mask layer 310 containing a silicon oxide unit exposed on the surface thereof and baking the adhesive layer, the step (S114) of forming a resin layer on the adhesive layer, the step (S115) of disposing and pressing a patterned stamp, the step (S116) of applying light, and the step (S117) of detaching the clamp is performed again. Thereafter, the step (S120) of determining whether the formed resin pattern is defective is performed, and then the step (S140) of forming a metal pattern if the resin pattern is not defective (N or no) is performed.

Figure 4A:
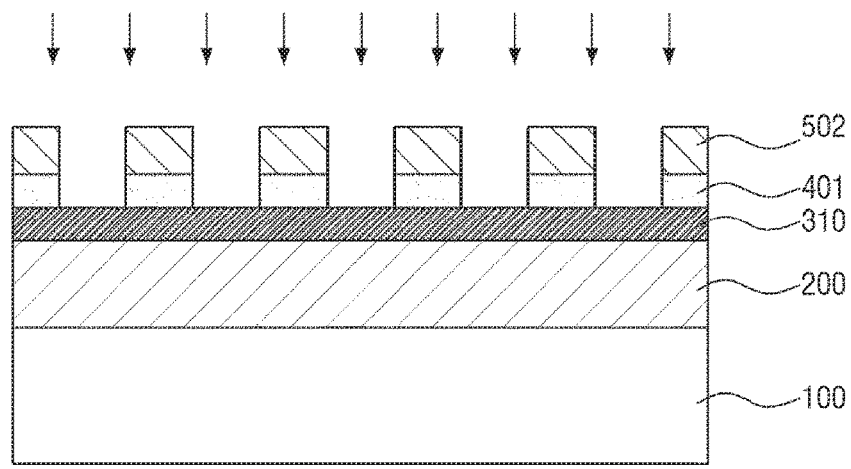
Figure 4B:
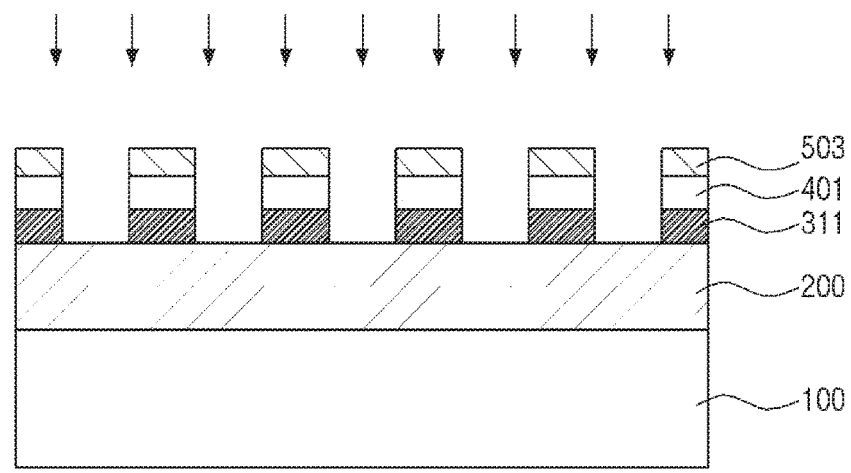

FIGS. 4A, 4B, and 4C are cross-sectional views showing a process of forming a metal pattern of FIG. 1 in a stepwise manner.

Referring to FIGS. 4A to 4C, first, a residual film layer of a resin layer and an adhesive layer is etched (S141) (hereinafter, first etching step). Specifically, a resin layer 501, which is an exposed uppermost layer, is etched to remove a residual film layer, and the remaining resin layer and the exposed adhesive layer is further etched to remove a part of the adhesive layer, thereby forming a patterned resin layer 502 and a patterned adhesive layer 401 and exposing at least a part of a mask layer 310 therebeneath.

Next, the mask layer 310 is etched (S142) (hereinafter, second etching step). Specifically, the exposed mask layer 310 is etched using the patterned resin layer 502 and the patterned adhesive layer 401 as a hard mask, thereby forming a patterned mask layer 311 and exposing at least a part of a metal layer 200 therebeneath. Simultaneously, at least a part of the patterned resin layer 502 used as the hard mask, or the patterned resin layer 502 and at least a part of the patterned adhesive layer 401 is consumed in the second etching step (S142) to be removed.

Next, the metal layer 200 is etched (S143) (hereinafter, third etching step). Specifically, the exposed metal layer 200 is etched using the patterned resin layer 503, the patterned adhesive layer 401 and the patterned mask layer as a hard mask, thereby forming a wire grid pattern 201. As described above, since the patterned mask layer 311 used as a hard mask has high etching selectivity to the metal layer 200, it is possible to control a precise pattern.

The first to third etching steps (S141, S142, and S143) may be sequentially performed while changing the process conditions, such as the kind of gas and/or plasma used in etching, etching temperature, etching time, and the like in consideration of the material of the exposed uppermost layer and the etching selectivity thereof. However, in some embodiments, the first to third etching steps (S141, S142, and S143) may also be substantially continuously performed without distinction.

Hereinafter, a method of manufacturing a wire grid pattern according to another exemplary embodiment will be described. However, for purposes of simplicity, descriptions of configurations thereof substantially identical or similar to those of the above-mentioned method of manufacturing a wire grid pattern according to an exemplary embodiment will be omitted, which is clearly understood to those skilled in the art.

Figure 5:
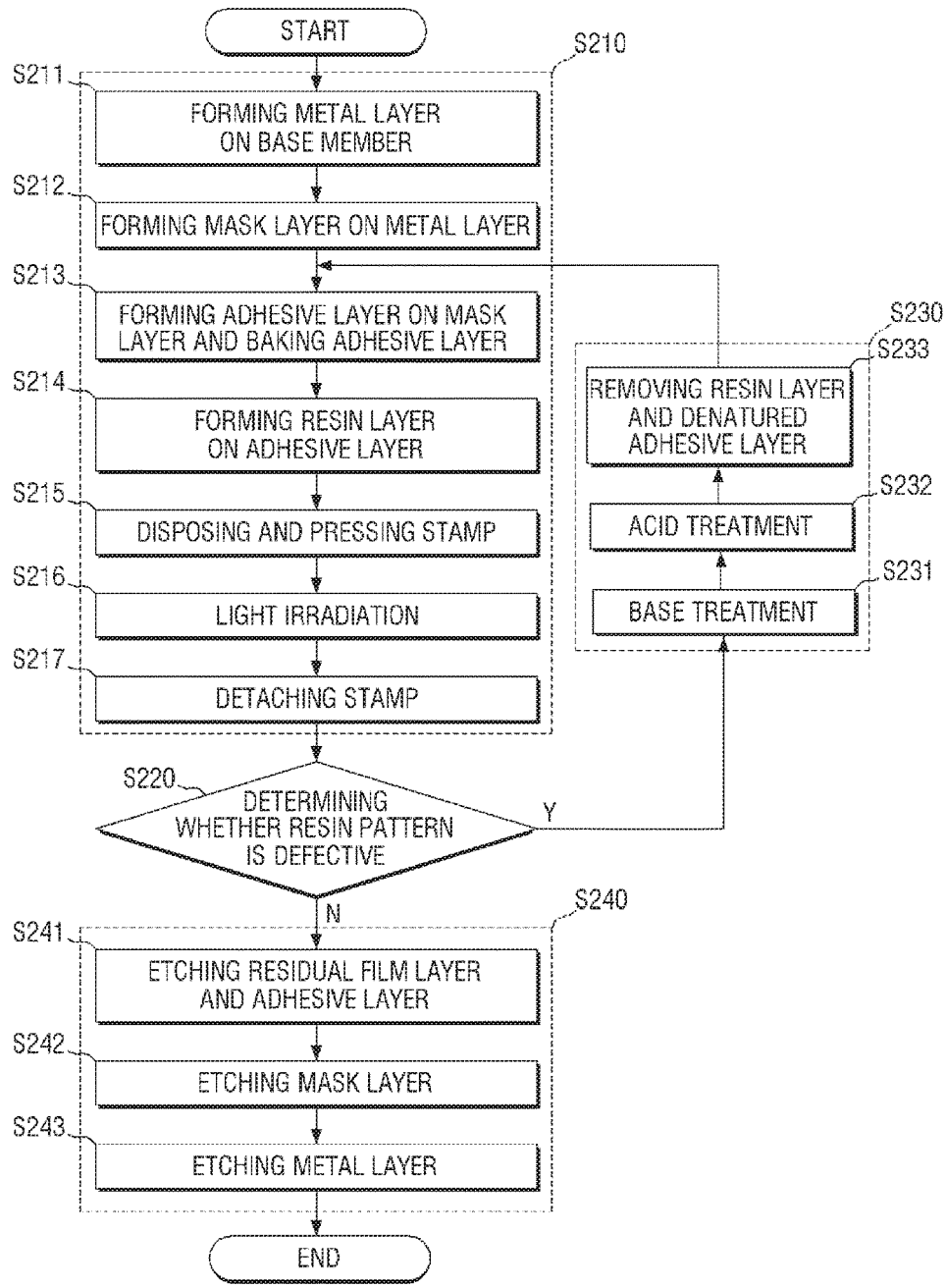
FIG. 5 is a flowchart showing a method of manufacturing a wire grid pattern according to another exemplary embodiment.
Figure 6A:
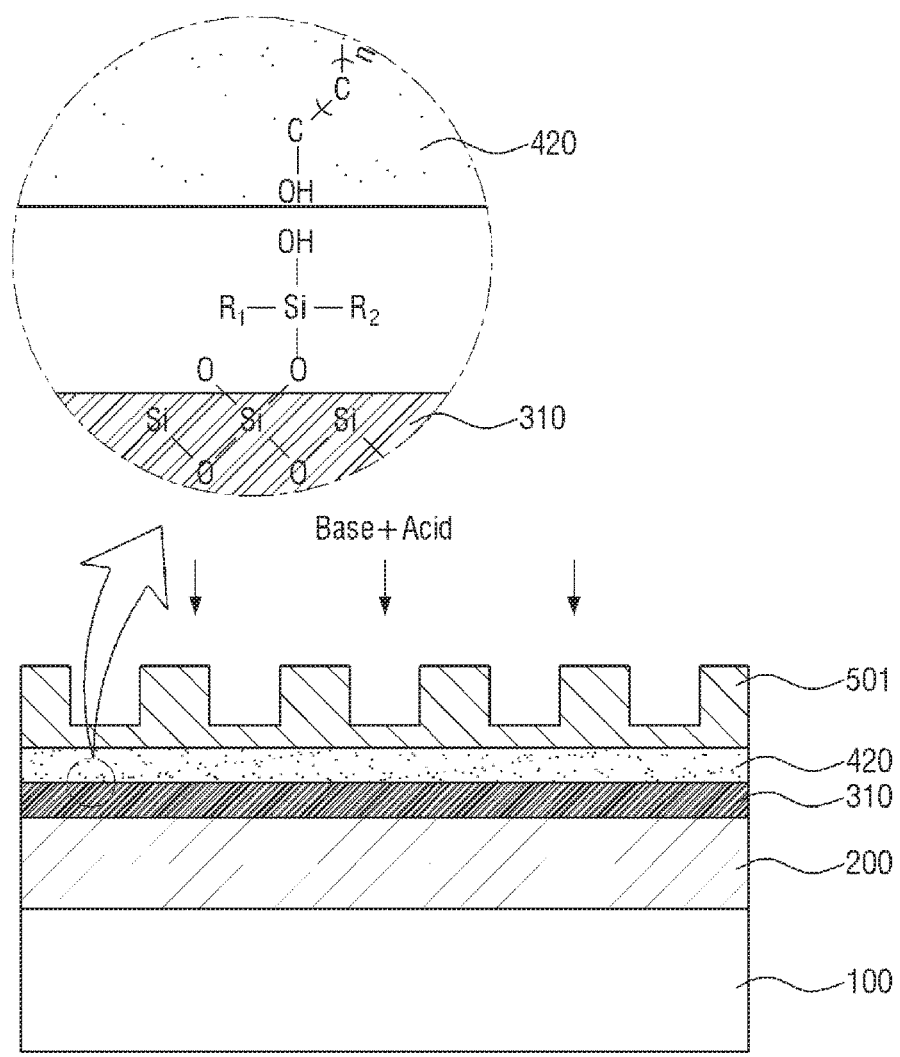

FIG. 5 is a flowchart showing a method of manufacturing a wire grid pattern according to another exemplary embodiment. FIGS. 6A, 6B, and 6C are cross-sectional views showing a process of removing a resin pattern of FIG. 5 in a stepwise manner.

Referring to FIG. 5, the method of manufacturing a wire grid pattern according to another exemplary embodiment includes the steps of: forming a resin pattern (210); determining whether the resin pattern is defective (S220); removing the resin pattern in order to perform a reworking when it is determined that the resin pattern is defective (S230); and forming a metal pattern (S240).

The step (S210) of forming a resin pattern may includes the steps of: preparing a base member; forming a metal layer on the base member (S211); forming a mask layer on the metal layer (S212); forming an adhesive layer containing a silane coupling agent on the mask layer and baking the adhesive layer (S213); forming a resin layer on the adhesive layer (S214); disposing and pressing a patterned stamp (S215); irradiating the resin layer with light (S216); and removing the stamp (S217). In some embodiments, the mask layer may be a multi-layer structure having a plurality of layers.

Meanwhile, the silane coupling agent according to another exemplary embodiment includes a compound represented by Chemical Formula 2-1 below.

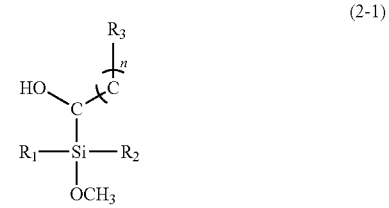

(2-1)

In the formula 2-1, $R_1$ and $R_2$ are each independently any one of $-CH_3$, $-OCH_2CH_3$, $-OCH_3$, and a functional group represented by Chemical Formula 2-2 below.

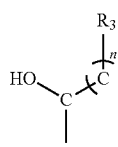

(2-2)

In the formulae 2-1 and 2-2, $R_3$ is any one of an acrylate group and a methacrylate group, and n is an integer of 1 to 10.

A composition containing the silane coupling agent is applied onto the mask layer in which a hydroxyl group is exposed on the surface thereof, and is then baked to induce a covalent bond between one molecular end of the silane coupling agent and at least a part of the hydroxyl group of the surface of the mask layer as well as to remove a solvent in the composition, thereby forming a strong bond between the adhesive layer and the mask layer.

If it is determined that the resin pattern is defective (Y or yes) after forming the resin pattern, a rework process including the step of removing the defective resin pattern is performed.

FIGS. 6A, 6B, and 6C are cross-sectional views showing a process of removing a resin pattern of FIG. 5 in a stepwise manner.

Referring to FIG. 5, the step (S230) of removing a resin pattern includes a base treatment step (S231), an acid treatment step (S232), and a step (S233) of removing a resin layer and a denatured adhesive layer.

Referring to FIGS. 5 and 6A, an adhesive layer is treated with a base reagent (S231). When the adhesive layer is treated with the base reagent, brook rearrangement may occur in the silane coupling agent molecule in the adhesive layer, but exemplary embodiments are not limited thereto.

Next, the adhesive layer is treated with an acid reagent (S232). The adhesive layer is denatured by the step of treating the adhesive layer with the base reagent and the step of treating the adhesive layer with the acidic reagent, and, as shown in FIG. 6A, a part of the molecular chain derived from the silane coupling agent molecule is cut, and thus the adhesive layer may be decomposed.

Specifically, when the bond between silicon (Si) and an oxygen group of end of an alkyl chain is cut, a silicon-centered molecular unit may remain while maintaining a covalent bond with a mask layer 310 therebeneath, and an alkyl chain unit occupying a majority of the adhesive layer 420 may be detached from the surface of the mask layer 310 while maintaining a covalent bond with a resin layer 501 thereon. That is, due to the denaturation of the adhesive layer 420, the mask layer 310 and the resin layer 501, which has been bonded to each other through the adhesive layer 420, lose a boding force, and thus a rework for removing the resin layer 501 may be easily performed.

Next, referring to FIGS. 5, 6B, and 6C, the resin layer and the denatured adhesive layer are removed (S233), and a base member 100, a metal layer 200, and a mask layer 310 are provided in a state in which the adhesive layer and the resin layer were removed.

As described above with reference to FIG. 6A, the resin layer 501 and alkyl chain molecules in the adhesive layer 420 having lost a bonding force with the mask layer 310 can be easily removed. In this case, a part of a silane coupling agent molecule including a silicon oxide unit may remain on the surface of the mask layer 310. A hydroxyl group of end of the remaining silane coupling agent molecule including a silicon oxide unit can be substantially chemically bonded with the hydroxyl group exposed on the surface of the first mask layer 300. Therefore, the mask layer 310, in which a silicon oxide unit is exposed on the surface thereof, can form a covalent bond with the adhesive layer containing a silane coupling agent and formed in the rework process although the surface composition of the mask layer 310 becomes different from that of the first mask layer 300.

Next, the step (S210) of forming a resin pattern is performed again, and then the step (S220) of determining whether the formed resin pattern is defective is performed. In this case, if the resin pattern is not defective (N or no), the step (S240) of forming a metal pattern including the steps of: etching the adhesive layer and a residual film layer of the resin layer (S241); etching the mask layer (S242); and etching the metal layer (S243) is performed, thereby forming a wire grid pattern.

Hereinafter, a method of manufacturing a wire grid pattern according to still another exemplary embodiment will be described.

Figure 8A:
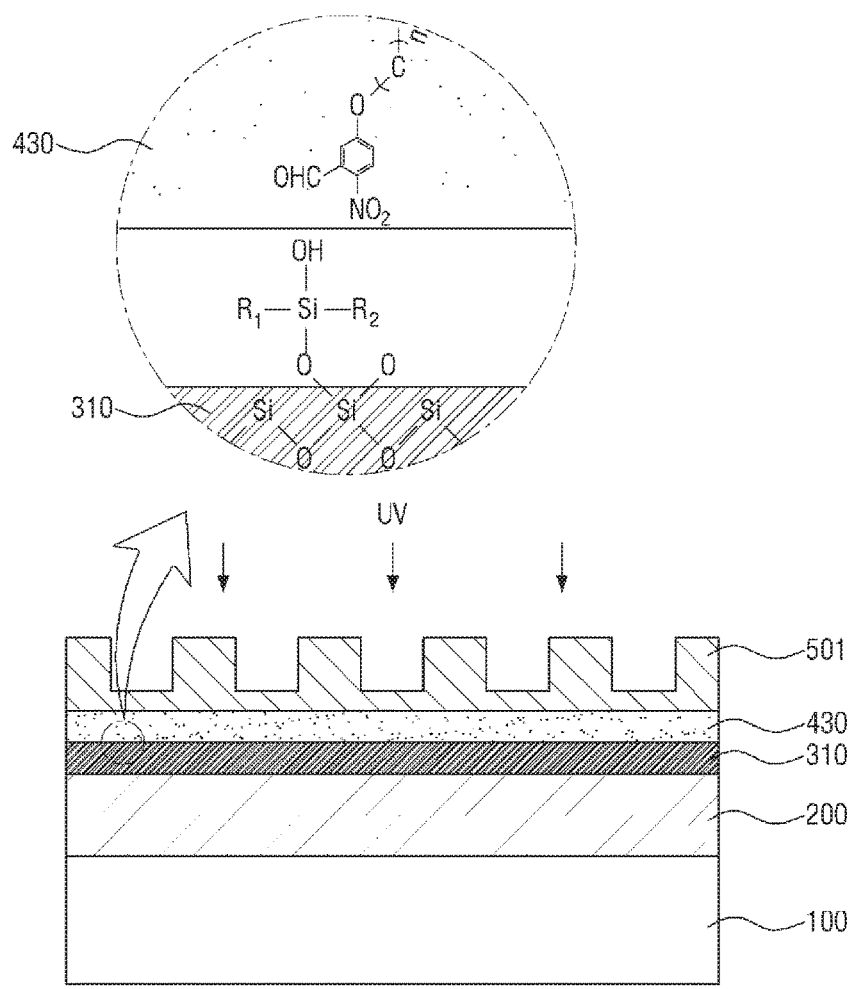
FIG. 8A, FIG. 8B, and FIG. 8C are cross-sectional views showing a process of removing a resin pattern of FIG. 7 in a stepwise manner.
Figure 8B:
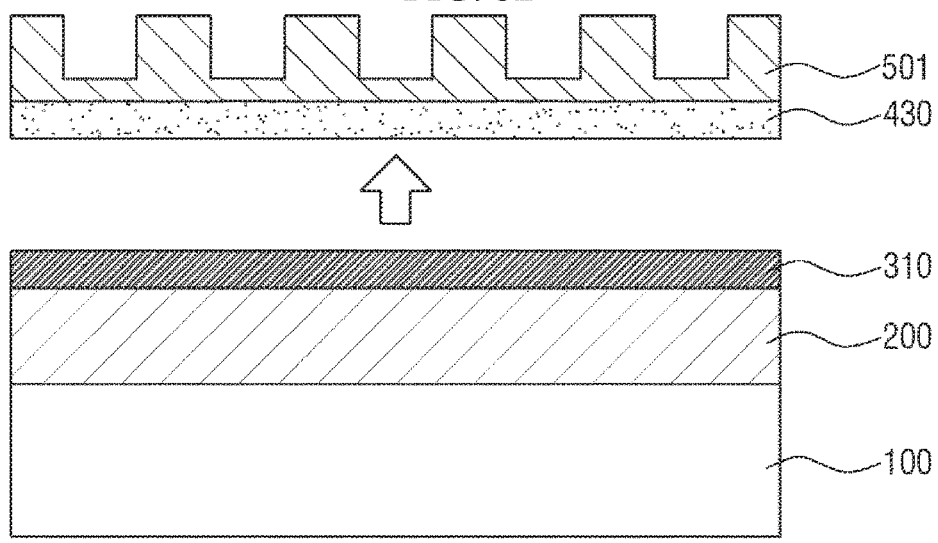
Figure 8C:
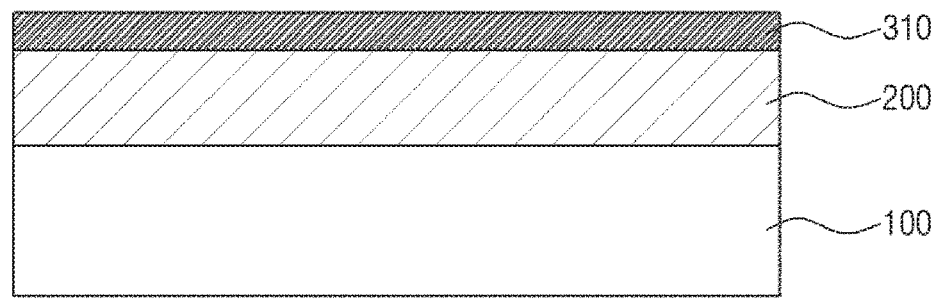

FIG. 7 is a flowchart showing a method of manufacturing a wire grid pattern according to still another exemplary embodiment. FIGS. 8A, 8B, and 8C are cross-sectional views showing a process of removing a resin pattern of FIG. 7 in a stepwise manner.

Referring to FIG. 7, the method of manufacturing a wire grid pattern according to still another exemplary embodiment includes the steps of: forming a resin pattern (S310); determining whether the resin pattern is defective (S320); removing the resin pattern in order to perform a reworking when it is determined that the resin pattern is defective (S330); and forming a metal pattern (S340).

The step (S310) of forming a resin pattern may includes the steps of: preparing a base member; forming a metal layer on the base member (S311); forming a mask layer on the metal layer (S312); forming an adhesive layer containing a silane coupling agent on the mask layer and baking the adhesive layer (S313); forming a resin layer containing a photoinitiator on the adhesive layer (S314); disposing and pressing a patterned stamp (S315); irradiating the resin layer with light (S316) (hereinafter, first light irradiation step); and removing the stamp (S317).

Meanwhile, the silane coupling agent according to still another exemplary embodiment includes a compound represented by Chemical Formula 3-1 below.

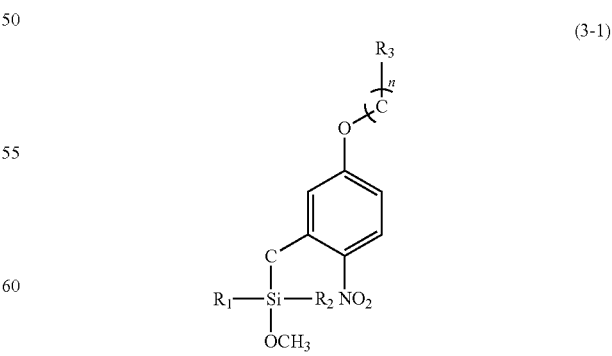

(3-1)

In the formula 3-1, $R_1$ and $R_2$ are each independently any one of —$CH_3$, —$OCH_2CH_3$, —$OCH_3$, and a functional group represented by Chemical Formula 3-2 below.

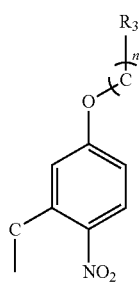

(3-2)

In the formulae 3-1 and 3-2, $R_3$ is any one of an acrylate group and a methacrylate group, and n is an integer of 1 to 10.

A composition containing the silane coupling agent is applied onto the mask layer in which a hydroxyl group is exposed on the surface thereof, and is then baked to induce a covalent bond between one molecular end of the silane coupling agent and at least a part of the hydroxyl group of the surface of the mask layer as well as to remove a solvent in the composition, thereby forming a strong bond between the adhesive layer and the mask layer.

Meanwhile, in an exemplary embodiment, the light used in the first light irradiation step (S316) may be UV light having a wavelength of 240 nm to 260 nm or IR having a wavelength equal to or longer than the wavelength of UV. The resin layer containing a photoinitiator may be cured by the irradiation of light having a wavelength capable of inducing the curing with the photoinitiator, and the cured resin layer can maintain the formed pattern shape even after detaching the stamp and can function as a hard mask by removing the fluidity of the resin layer.

Further, a covalent bond is induced between an acrylate group of one molecular end of the silane coupling agent in the adhesive layer and an acrylate group in the resin layer by the light irradiation, thereby forming a strong bond between the adhesive layer and the cured resin layer.

If it is determined that the resin pattern is defective (Y or yes) after forming the resin pattern, a rework process including the step (S330) of removing the defective resin pattern is performed.

FIGS. 8A, 8B, and 8C are cross-sectional views showing a process of removing a resin pattern of FIG. 7 in a stepwise manner.

Referring to FIG. 7, the step (S330) of removing a resin pattern includes a UV irradiation step (S331) and a step (S332) of removing a resin layer and a denatured adhesive layer.

Referring to FIGS. 7 and 8A, an adhesive layer is irradiated with UV (S331) (hereinafter, second light irradiation step). FIG. 8A shows a case that light is emitted from above, but light may be emitted from below. The UV used in the second light irradiation step (S331) may have a different wavelength from the UV used in the first light irradiation step (S316). In an exemplary embodiment, the UV used in the second light irradiation step (S331) may be UV light having a wavelength of 350 nm to 370 nm. The adhesive layer is denatured by the second light irradiation step (S331), and, as shown in FIG. 8A, a part of the molecular chain derived from the silane coupling agent molecule is cut, and thus the adhesive layer 430 may be decomposed.

Specifically, when the bond between silicon (Si) and a methyl group located at the 1-position of an ortho-nitrobenzyl group is cut, a silicon-centered molecular unit may remain while maintaining a covalent bond with a mask layer 310 therebeneath, and a nitrobenzene unit and an alkyl chain unit ether-bonded to the nitrobenzene unit, which occupy a majority of the adhesive layer 430, may be detached from the surface of the mask layer 310 while maintaining a covalent bond with a resin layer 501 thereon. That is, due to the denaturation of the adhesive layer 430, the mask layer 310 and the resin layer 501, which has been bonded to each other through the adhesive layer 430, lose a boding force, and thus a rework for removing the resin layer 501 may be easily performed.

Next, referring to FIGS. 7, 8B, and 8C, the resin layer and the denatured adhesive layer are removed (S332), and a base member 100, a metal layer 200, and a mask layer 310 are provided in a state in which the adhesive layer and the resin layer were removed.

As described above with reference to FIG. 8A, the resin layer 501 and alkyl chain molecules containing a nitrobenze unit in the adhesive layer 430 having lost a bonding force with the surface of the mask layer 310 can be easily removed. In this case, a part of a silane coupling agent molecule including a silicon oxide unit may remain on the surface of the mask layer 310. A hydroxyl group of end of the remaining silane coupling agent molecule including a silicon oxide unit can be substantially chemically bonded with the hydroxyl group exposed on the surface of the first mask layer 300. Therefore, the mask layer 310, in which a silicon oxide unit is exposed on the surface thereof, can form a covalent bond with the adhesive layer containing a silane coupling agent and formed in the rework process although the surface composition of the mask layer 310 becomes different from that of the first mask layer 300.

Next, the step (S310) of forming a resin pattern is performed again, and then the step (S320) of determining whether the formed resin pattern is defective is performed. In this case, if the resin pattern is not defective (N or no), the step (S340) of forming a metal pattern including the steps of: etching the adhesive layer and a residual film layer of the resin layer (S341); etching the mask layer (S342); and etching the metal layer (S343) is performed, thereby forming a wire grid pattern.

As described above, according to the method of manufacturing a wire grid pattern according to an embodiment, the resin layer is strongly bonded with the substrate by the silane coupling agent, thereby minimizing the stripping of the resin pattern even during removing the stamp.

Further, since the silane coupling agent is denatured by ultraviolet light or under basic and acidic conditions to lose bonding force, the bonding force between the substrate and the resin layer can be easily controlled, thereby increasing the production yield of a wire grid pattern as well as improving the processibility of a rework process.

Moreover, since a functional group capable of forming a covalent group together with the silane coupling agent is exposed on the surface of the substrate from which the resin layer was removed, the bonding force between the substrate and the silane coupling agent becomes excellent.

Although certain exemplary embodiments and implementations have been described herein, other embodiments and modifications will be apparent from this description. Accordingly, the inventive concept is not limited to such embodiments, but rather to the broader scope of the presented claims and various obvious modifications and equivalent arrangements.

What is claimed is:

1. A method of manufacturing a wire grid pattern, comprising:

providing a laminate comprising a base member, a metal layer disposed on the base member, a mask layer disposed on the metal layer and containing a metal oxide, an adhesive layer disposed on the mask layer, and a patterned resin layer disposed on the adhesive layer and formed by contacting with a patterned stamp and irradiating with a first light; determining if the patterned resin layer is defective;

irradiating the laminate with a second light when the patterned resin layer is determined to be defective to release the adhesive layer and the patterned resin layer, recoating the adhesive layer and reforming the patterned resin layer by contacting with a patterned stamp and irradiating with the first light; and etching the metal layer using the patterned resin layer as a hard mask when the patterned resin layer is not defective, wherein the adhesive layer contains a compound represented by Chemical Formula 3-1 below:

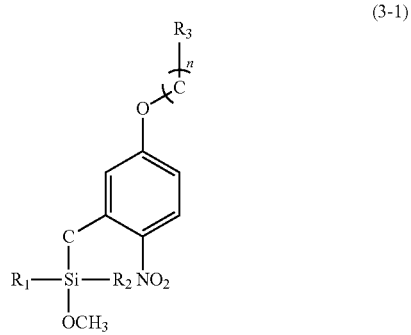

(3-1)

wherein in the formula 3-1, $R_1$ and $R_2$ are each independently any one of —$CH_3$, —$OCH_2CH_3$, —$OCH_3$, and a functional group represented by Chemical Formula 3-2 below,

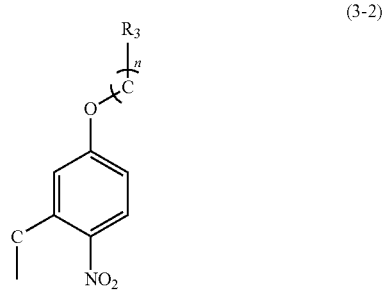

(3-2)

and wherein in the formulae 3-1 and 3-2, $R_3$ is any one of an acrylate group and a methacrylate group, and n is an integer of 1 to 10.

2. The method of claim 1,
wherein the providing of the laminate comprises:
preparing the base member;
forming the metal layer on the base member;
forming the mask layer containing a metal oxide on the metal layer;
forming the adhesive layer on the mask layer and baking the adhesive layer;
forming the resin layer on the adhesive layer;
transferring a pattern to the resin layer using the patterned stamp; and
irradiating the adhesive layer and the resin layer with the first light.

3. The method of claim 1, wherein the second light has a wavelength of 350 nm to 370 nm.

4. The method of claim 1, wherein the patterned resin layer comprises a photoinitiator.

5. The method of claim 1, wherein a wavelength of the first light is different from a wavelength of the second light.

6. The method of claim 1, wherein the metal layer comprises one or more materials selected from the group consisting of any one metal of aluminum, gold, silver, copper, chromium, iron, nickel, molybdenum, and titanium, an oxide of the any one metal, and an alloy of the any one metal.

7. A method of manufacturing a wire grid pattern, comprising:
providing a laminate comprising a base member, a metal layer disposed on the base member, a mask layer disposed on the metal layer and containing a metal oxide, an adhesive layer disposed on the mask layer, and a patterned resin layer disposed on the adhesive layer and formed by contacting with a patterned stamp and irradiating with a first light; determining if the patterned resin layer is defective;

irradiating the laminate with a second light and treating the laminate with an acid when the patterned resin layer is determined to be defective to release the adhesive layer and the patterned resin layer, recoating the adhesive layer and reforming the patterned resin layer by contacting with a patterned stamp and irradiating with the first light; and etching the metal layer using the patterned resin layer as a hard mask when the patterned resin layer is not defective, wherein the adhesive layer comprises a compound represented by Chemical Formula 1-1 below:

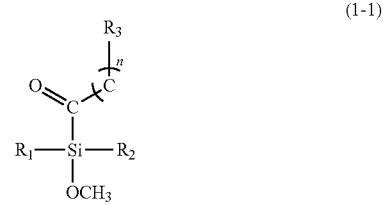

(1-1)

wherein in the formula 1-1, $R_1$ and $R_2$ are each independently any one of —$CH_3$, —$OCH_2CH_3$, —$OCH_3$, and a functional group represented by Chemical Formula 1-2 below,

(1-2)

and wherein in the formulae 1-1 and 1-2, $R_3$ is any one of an acrylate group and a methacrylate group, and n is an integer of 1 to 10.

8. The method of claim 7, wherein the second light has a wavelength of 500 nm to 600 nm.

\* \* \* \* \*